United States Patent
Johnson

(10) Patent No.: US 12,064,377 B2
(45) Date of Patent: *Aug. 20, 2024

(54) BREATH DEFLECTOR AND METHOD OF USE

(71) Applicant: Corey B. Johnson, Hyrum, UT (US)

(72) Inventor: Corey B. Johnson, Hyrum, UT (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/821,949

(22) Filed: Aug. 24, 2022

(65) Prior Publication Data

US 2022/0401264 A1   Dec. 22, 2022

Related U.S. Application Data

(63) Continuation of application No. 16/794,206, filed on Feb. 18, 2020, now Pat. No. 11,446,181.

(60) Provisional application No. 62/809,352, filed on Feb. 22, 2019.

(51) Int. Cl.
*A61F 9/02*    (2006.01)
*A42B 3/18*    (2006.01)
*A42B 3/20*    (2006.01)
*A42B 3/22*    (2006.01)

(52) U.S. Cl.
CPC .............. *A61F 9/029* (2013.01); *A42B 3/185* (2013.01); *A42B 3/20* (2013.01); *A42B 3/228* (2013.01)

(58) Field of Classification Search
CPC ........... A61F 9/029; A42B 3/185; A42B 3/20; A42B 3/228; A42B 3/24
See application file for complete search history.

(56) References Cited

U.S. PATENT DOCUMENTS

| | | | |
|---|---|---|---|
| 4,016,919 A | 4/1977 | Zmijewski | 160/130 |
| 5,046,492 A | 9/1991 | Stackhouse et al. | 128/200.27 |
| 5,797,146 A | 8/1998 | Atich | 2/424 |
| 5,934,599 A | 8/1999 | Hammerslag | 242/396.1 |
| 5,956,119 A | 9/1999 | Gibbs | 351/158 |
| D447,605 S | 9/2001 | Kalhok | D29/107 |
| 6,289,558 B1 | 9/2001 | Hammerslag | 24/68 |
| D450,160 S | 11/2001 | Kalhok | D29/107 |
| D451,643 S | 12/2001 | Kalhok | D29/107 |
| D452,592 S | 12/2001 | Kalhok | D29/107 |
| D475,815 S | 6/2003 | Kalhok | D29/107 |
| 6,606,751 B1 | 8/2003 | Kalhok et al. | 2/424 |
| 6,644,308 B2 | 11/2003 | Kalhok et al. | 128/201.24 |
| 6,742,192 B1 | 6/2004 | Song | 2/422 |
| D497,223 S * | 10/2004 | Kalhok | D29/107 |
| 6,854,464 B2 | 2/2005 | Mukaiyama et al. | 128/206.17 |
| 6,859,946 B2 | 3/2005 | Fournier et al. | 2/424 |

(Continued)

*Primary Examiner* — Khaled Annis
(74) *Attorney, Agent, or Firm* — Michael R. Schramm

(57) ABSTRACT

The present invention is a breath deflector apparatus and method of use. The apparatus comprises a breadth deflector preferably connected to a goggle frame, with the goggle frame being connected to an adjustable securement device that is adjustably connected to a preferably cold weather helmet. The breath deflector apparatus is preferably adjustable by twisting a knob mounted to the front of the helmet and is preferably adapted such that once adjusted, the breath deflector moves in synchronization or unison with the movement of a user's head within the helmet and thus prevents loss of securement and maladjustment of the breath deflector while using the breath deflector and during movement of the user's head.

20 Claims, 8 Drawing Sheets

(56) References Cited

U.S. PATENT DOCUMENTS

| | | | |
|---|---|---|---|
| 7,003,802 B2 | 2/2006 | Broersma | 2/9 |
| D517,249 S * | 3/2006 | Kalhok | D29/122 |
| 7,120,940 B2 | 10/2006 | Fournier et al. | 2/424 |
| 7,591,050 B2 | 9/2009 | Hammerslag | 24/68 |
| 7,814,578 B2 | 10/2010 | Kosel et al. | 2/422 |
| 7,937,779 B2 | 5/2011 | Klotz et al. | 2/416 |
| 8,407,819 B2 | 4/2013 | Chen | 2/424 |
| 8,707,471 B2 | 4/2014 | Chen | 2/424 |
| 10,123,589 B2 | 11/2018 | Soderberg et al. | A43C 11/00 |
| D835,898 S | 12/2018 | Lovett | D2/978 |
| 10,434,325 B2 * | 10/2019 | Tapper | A61N 5/0616 |
| 11,229,254 B1 * | 1/2022 | Matteucci | A42B 3/20 |
| 11,446,181 B2 * | 9/2022 | Johnson | A61F 9/029 |
| 11,510,814 B2 * | 11/2022 | Bouchard Fortin | A61F 9/028 |
| 2003/0209241 A1 | 11/2003 | Fournier | 128/201.22 |
| 2005/0036100 A1 | 2/2005 | Rice | 351/62 |
| 2005/0150028 A1 | 7/2005 | Broersma | 2/9 |
| 2006/0156517 A1 * | 7/2006 | Hammerslag | A43C 11/00 24/68 SK |
| 2006/0179553 A1 | 8/2006 | Kosel et al. | 2/422 |
| 2008/0060167 A1 * | 3/2008 | Hammerslag | A43C 11/165 24/714.6 |
| 2008/0189821 A1 | 8/2008 | Anderson | 2/9 |
| 2010/0071690 A1 | 3/2010 | Matich | 128/203.12 |
| 2010/0076532 A1 | 3/2010 | Matich | 607/109 |
| 2010/0139057 A1 | 6/2010 | Soderberg | 24/68 R |
| 2010/0299959 A1 * | 12/2010 | Hammerslag | A43C 11/16 36/50.5 |
| 2011/0167543 A1 * | 7/2011 | Kovacevich | F16G 11/12 2/417 |
| 2012/0260407 A1 | 10/2012 | Chen | 2/424 |
| 2013/0239303 A1 * | 9/2013 | Cotterman | A42B 3/08 2/417 |
| 2014/0358054 A1 * | 12/2014 | Capra | A61F 5/0102 602/16 |
| 2015/0014463 A1 * | 1/2015 | Converse | A61F 5/028 242/396.1 |
| 2015/0191326 A1 * | 7/2015 | Hall | B65H 75/4431 242/396.4 |
| 2016/0198803 A1 * | 7/2016 | Soderberg | A43C 11/165 12/142 LC |
| 2016/0270470 A1 * | 9/2016 | Hickman | A42B 3/08 |
| 2017/0216099 A1 * | 8/2017 | Saladino | A42B 3/185 |
| 2017/0245576 A1 * | 8/2017 | Hetzler | A42B 3/0473 |
| 2017/0265557 A1 | 9/2017 | Mercado | A42B 3/185 |
| 2017/0303620 A1 * | 10/2017 | Sicking | A63B 71/10 |
| 2017/0303643 A1 * | 10/2017 | Converse | A61C 7/026 |
| 2019/0008228 A1 | 1/2019 | Ramey | A24B 3/0406 |
| 2020/0179172 A1 | 6/2020 | Johnson | A61F 9/029 |
| 2020/0205499 A1 * | 7/2020 | Draper | G02C 3/003 |
| 2021/0245991 A1 | 8/2021 | Johnson | B65H 75/4492 |
| 2022/0302492 A1 * | 9/2022 | Visco | C03C 4/14 |
| 2023/0009215 A1 * | 1/2023 | Parizhsky | H04L 51/212 |

* cited by examiner

BREATH DEFLECTOR AND METHOD OF USE

CROSS REFERENCE TO RELATED APPLICATIONS

This nonprovisional utility patent application is a continuation of and claims the benefit under 35 USC § 120 to allowed co-pending U.S. application Ser. No. 16/794,206 filed Feb. 18, 2020, which claims the benefit under 35 USC § 119(e) of U.S. provisional application No. 62/809,352 filed Feb. 22, 2019, all of which are incorporated herein in their entirety by this reference.

FIELD OF THE INVENTION

The present invention relates to breath deflectors, and in particular, to breath deflectors that provide for convenient secure adjustment while preventing fogging of a face shield.

BACKGROUND OF THE INVENTION

Various means are known in the art for securing breath deflectors, especially for use in combination with a cold weather helmet. However, such means have typically been awkward in use and once secured, do not necessarily remain secured and so not move well in synchronization with the wearer. Further, certain adjusting means or tensioning means are known in the art. Examples of breath deflector apparatuses and adjustment means are disclosed in the following list of US patents and applications, all of which are expressly incorporated herein by reference: U.S. Pat. No. 4,016,919 to Zmijewski, U.S. Pat. No. 5,046,492 to Stackhouse, U.S. Pat. No. 5,797,146 to Matich, U.S. Pat. No. 5,934,599 to Hammerslag, U.S. Pat. No. 5,956,119 to Gibbs, U.S. Pat. No. 6,289,558 to Hammerslag, U.S. Pat. No. 6,606,751 to Kalhok, U.S. Pat. No. 6,644,308 to Kalhok, U.S. Pat. No. 6,742,192 to Song, U.S. Pat. No. 6,854,464 to Mukaiyama, U.S. Pat. No. 6,859,946 to Fournier, U.S. Pat. No. 7,003,802 to Broersma, U.S. Pat. No. 7,120,940 to Fournier, U.S. Pat. No. 7,591,050 to Hammerslag, U.S. Pat. No. 7,814,578 to Kosel, U.S. Pat. No. 7,937,779 to Klotz, U.S. Pat. No. 8,407,819 to Chen, U.S. Pat. No. 8,707,471 to Chen, U.S. Pat. No. 10,123,589 to Soderberg, D447,605 to Kalhok, D450,160 to Kalhok, D451,643 to Kalhok, D452,592 to Kalhok, D475,815 to Kalhok, D497,223 to Kalhok, D517,249 to Kalhok, D835,898 to Lovett, 20050150028 to Broersma, 20060179553 to Kosel, 20080189821 to Anderson, 20100071690 to Matich, and 20100076532 to Matich.

SUMMARY OF THE INVENTION

The present invention is a breath deflector apparatus and method of use. The apparatus comprises a breadth deflector preferably connected to a goggle frame, with the goggle frame being connected to an adjustable securement device that is adjustably connected to a preferably cold weather helmet. The breath deflector apparatus is preferably adjustable by twisting a knob mounted to the front of the helmet and is preferably adapted such that once adjusted, the breath deflector moves in synchronization or unison with the movement of a user's head within the helmet and thus prevents loss of securement and maladjustment of the breath deflector while using the breath deflector and during movement of the user's head.

DESCRIPTION OF DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1:
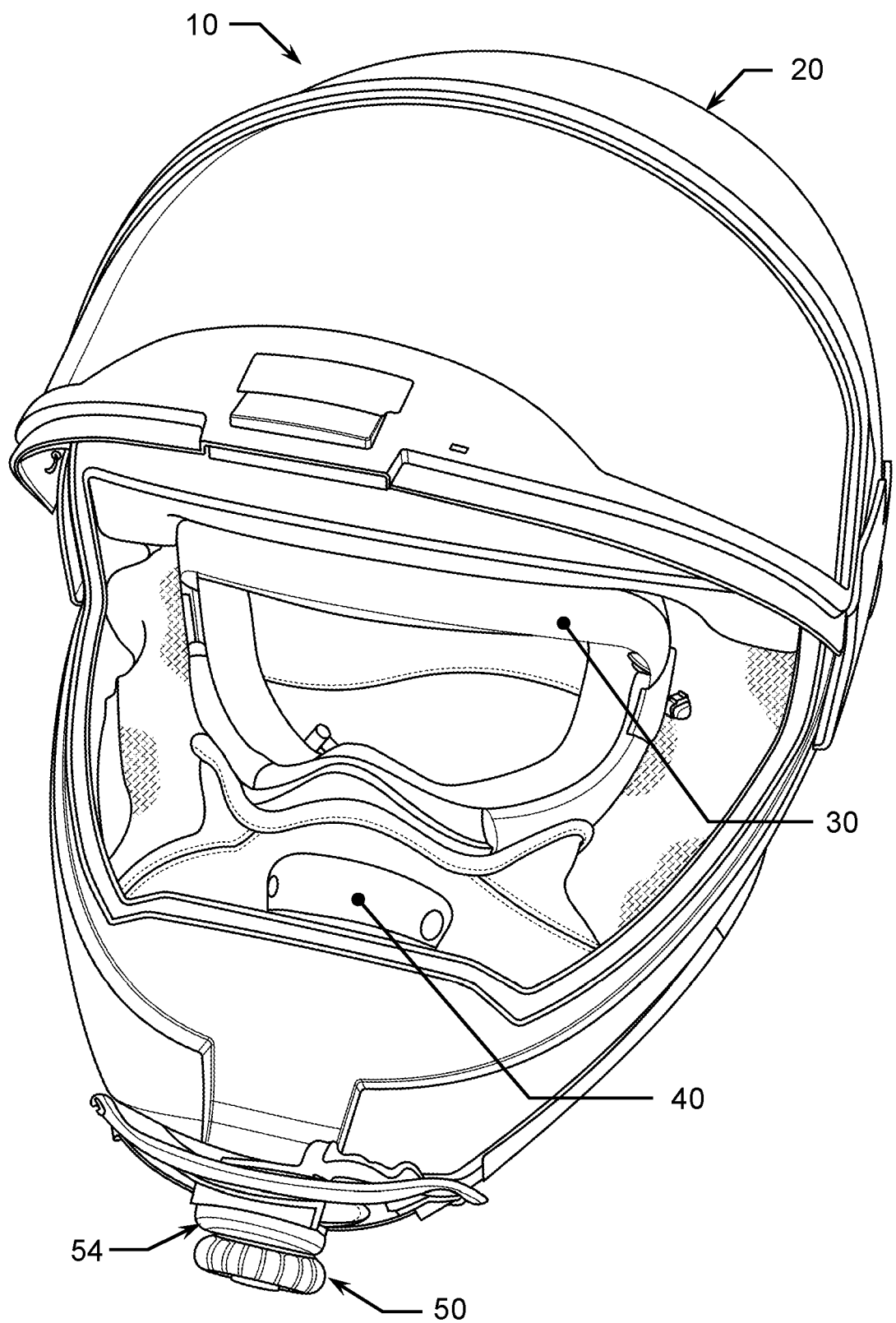
FIG. 1 is a first trimetric view of the breath deflector apparatus.
Figure 2:
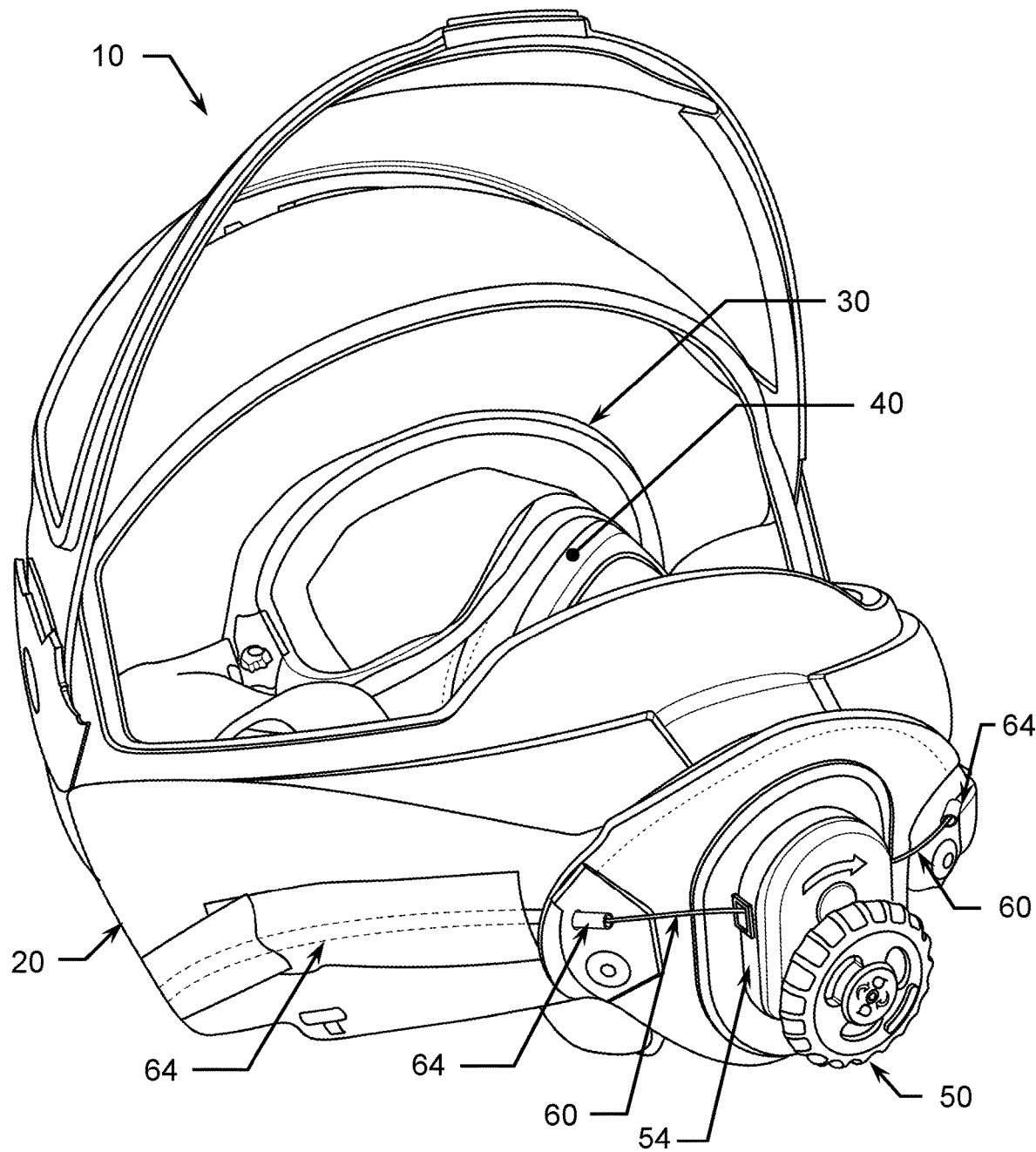
FIG. 2 is a second trimetric view of the breath deflector apparatus.
Figure 3:
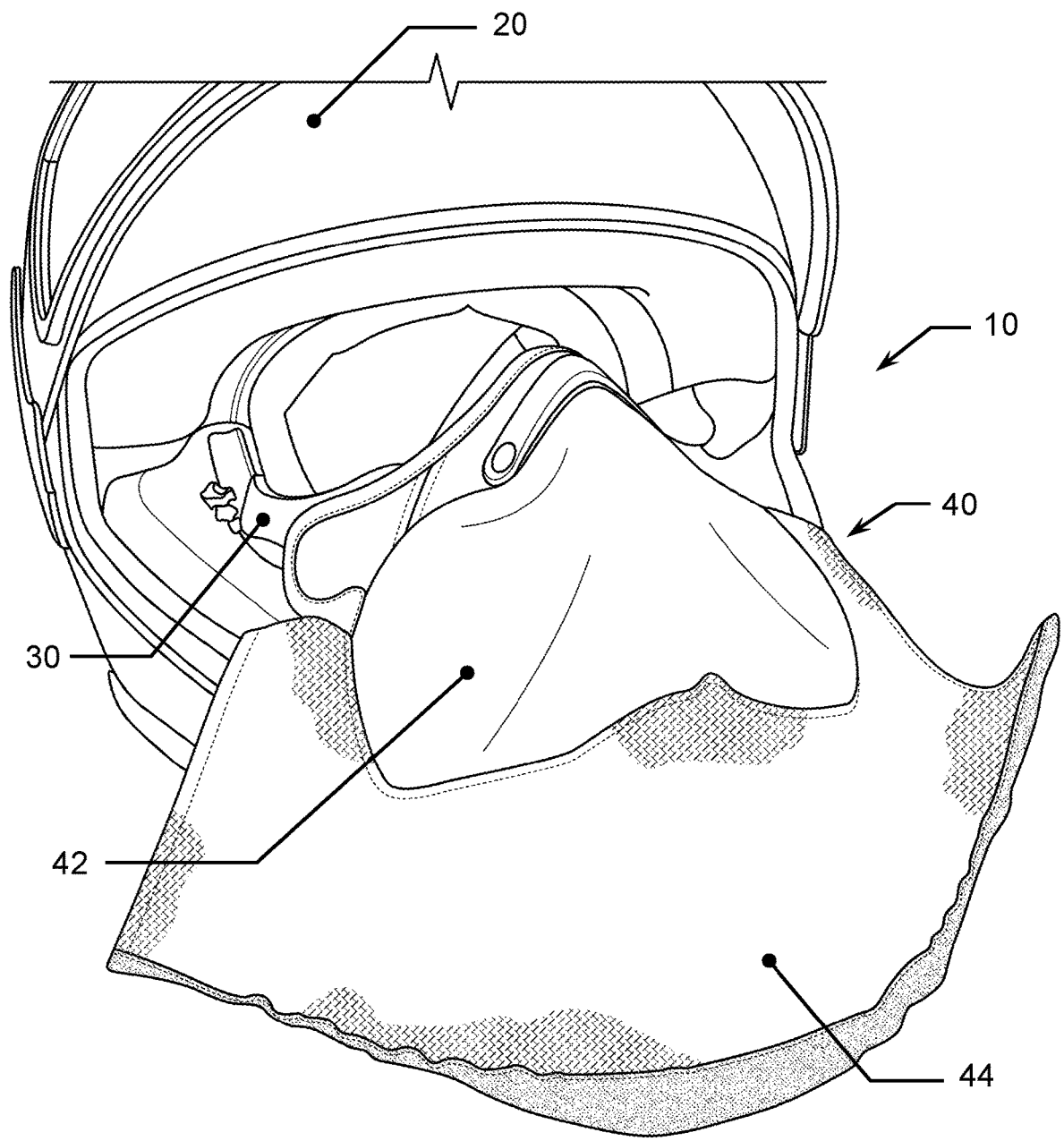
FIG. 3 is a trimetric view of the breath deflector apparatus with the breath deflector shown positioned partially outside of the helmet.
Figure 4:
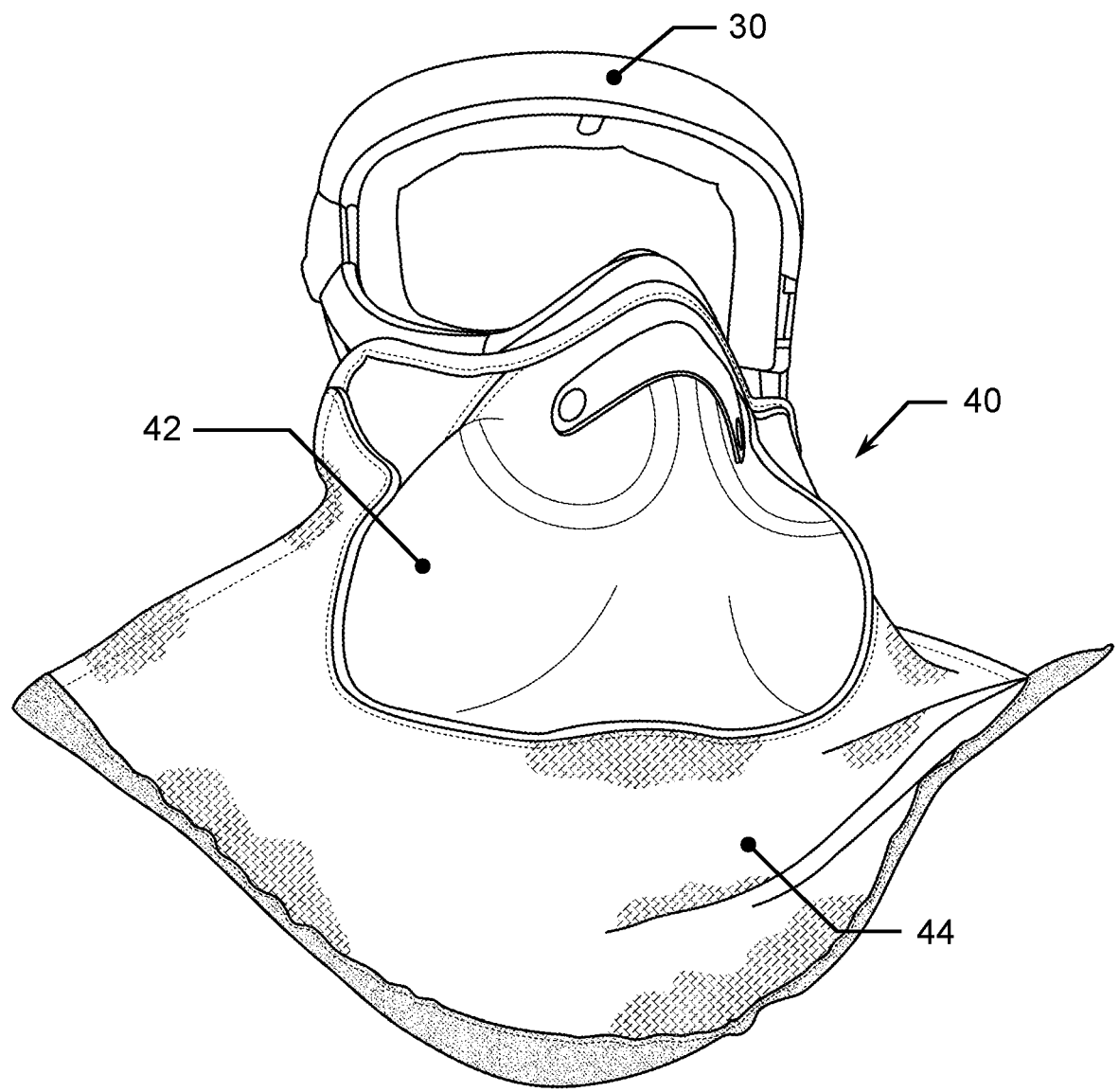
FIG. 4 is a trimetric view of the breath deflector mounted to a goggles frame.
Figure 5:
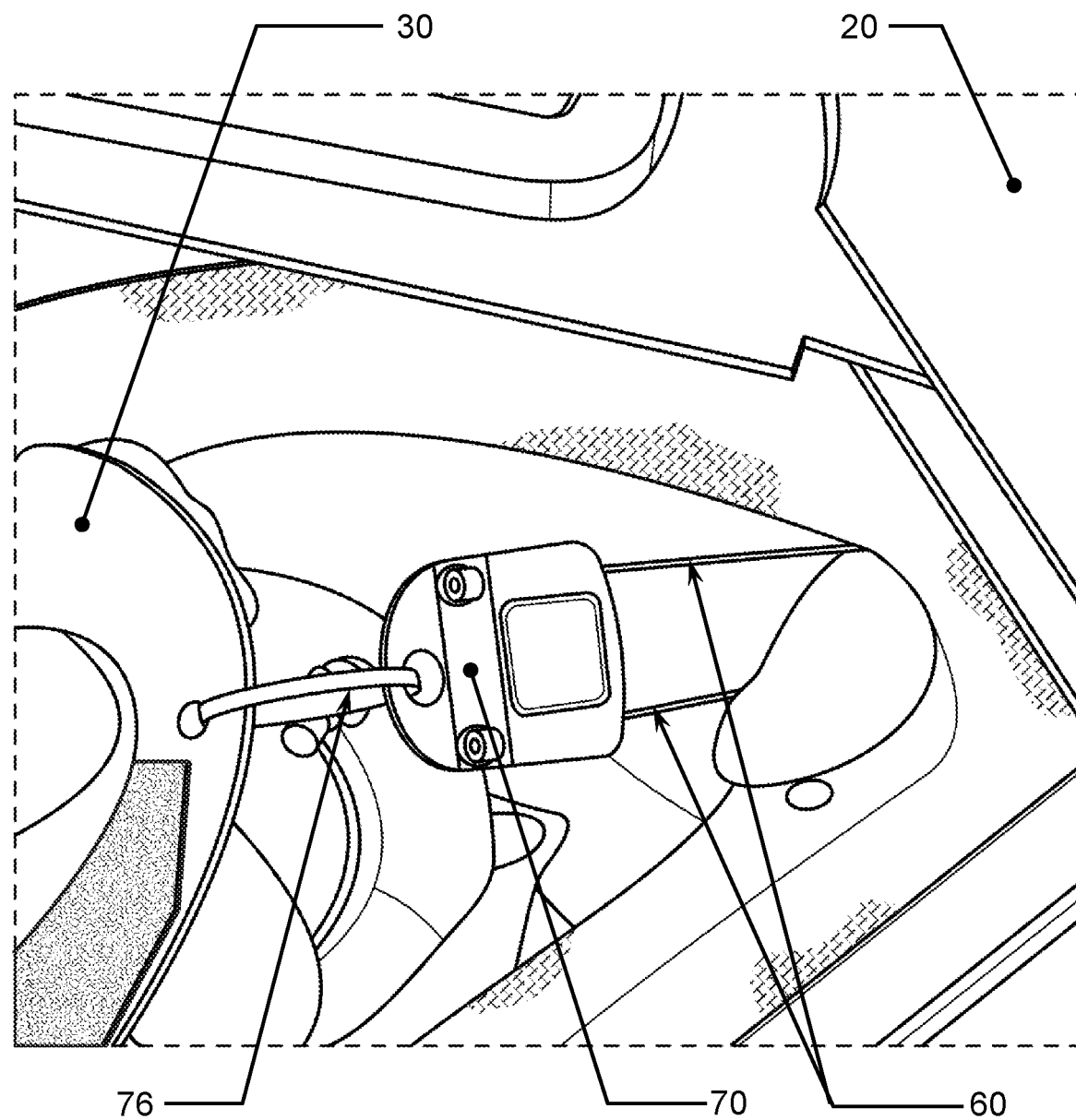
FIG. 5 is a close-up outside-helmet side view of the breath deflector apparatus showing a portion of the goggle frame connected to an adjustment cable.
Figure 6:
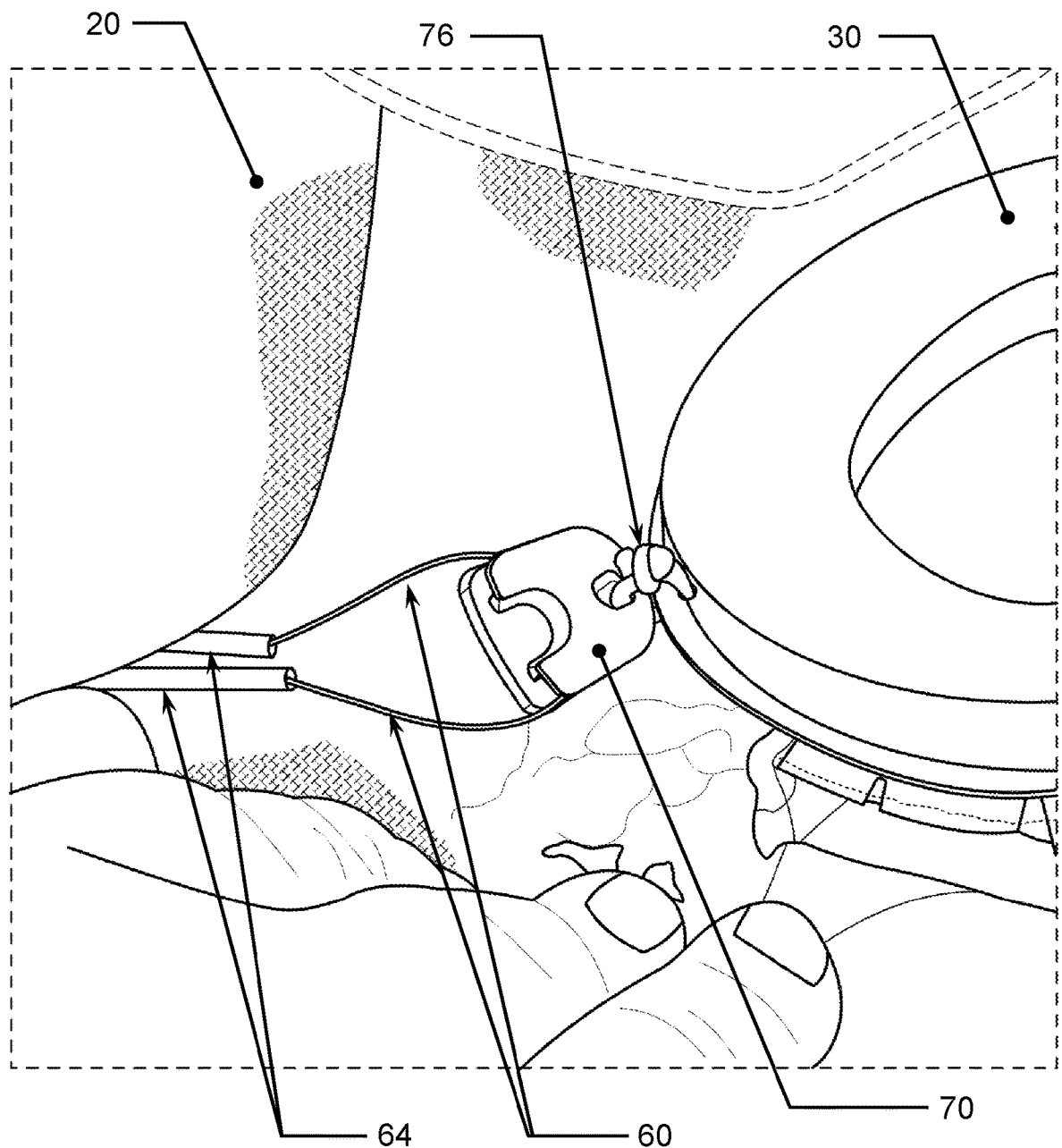
FIG. 6 is a close-up inside-helmet side view of the breath deflector apparatus showing a portion of the goggle frame connected to an adjustment cable and housing.
Figure 7:
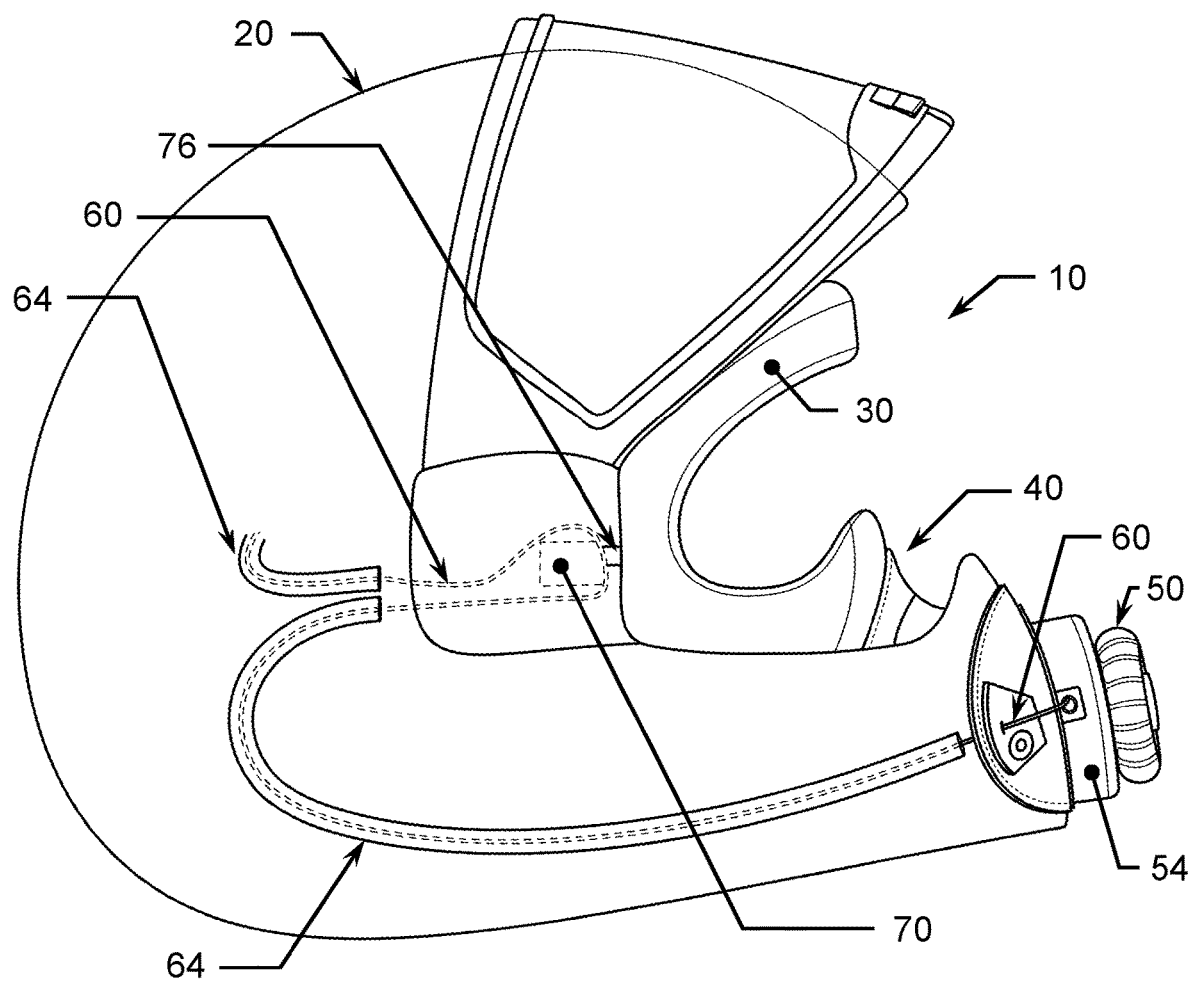
FIG. 7 is a schematic side view of the breath deflector apparatus illustrating the connection of an adjustment cable and housing to a goggle frame and an adjustment knob.
Figure 8:
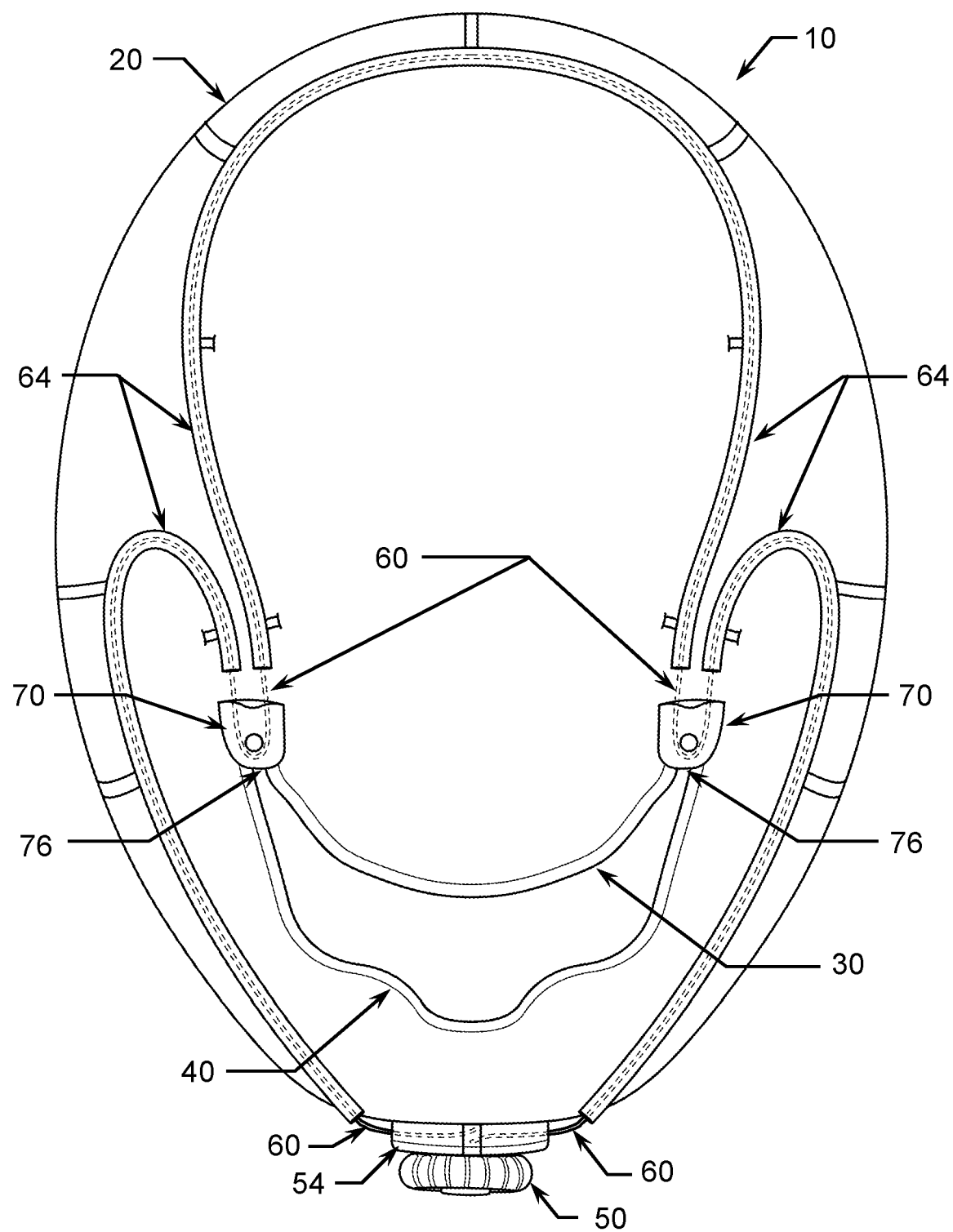
FIG. 8 is a schematic top view of the breath deflector apparatus illustrating the connection of an adjustment cable and housing to a goggle frame and an adjustment knob.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are included to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

In order to facilitate the understanding of the present invention in reviewing the drawings accompanying the specification, a feature table is provided below. It is noted that like features are like numbered throughout all of the figures.

FEATURE TABLE

| # | Feature | # | Feature |
|---|---------|---|---------|
| 10 | Breath deflector apparatus | 20 | Helmet |
| 30 | Goggle frame | 40 | Breath deflector |
| 42 | Mask | 44 | skirt |

FEATURE TABLE

| # | Feature | # | Feature |
|---|---|---|---|
| 50 | Adjustment knob | 54 | Cable spool |
| 60 | Cable | 64 | Cable housing |
| 70 | Pulley | 76 | Elastic cord |

Referring now to the drawings, a first embodiment of breath deflector apparatus 10 comprises breath deflector 40, goggle frame 30, elastic cords 76, pulleys 70, helmet 20, cable 60 (or like suitable tether), cable housings (tubes) 64, cable spool 54, and cable adjustment knob 50 (or like suitable adjustment device). Breath deflector 40 preferably defines formed but flexible nose and mouth mask 42 having preferably fabric skirt 44 attached to a lower end thereof. Goggle frame 30 preferably defines the frame portion (preferably without the lens) of a conventional pair of goggles. Elastic cords 76 and pulleys 70 are conventional commercially available cords and pulleys. Helmet 20 preferably defines a cold weather helmet such as a snowmobile helmet. Cable 60, cable housings (tubes) 64, cable spool 54, and cable adjustment knob 50 are preferably taken from a commercially available "BOA Fit System" (BOA) such as are commercially available from Boa Technology, Inc. having a headquarters located in Denver, CO (see BOA Technology, Inc. website).

Breath deflector apparatus 10 is assembled such that an upper edge of breath deflector 40 is connected to a lower edge of goggle frame 30, a first elastic cord 76 is connected to a first side of goggle frame 30 on a first end and to a first pulley 70 on a second end, a second elastic cord 76 is connected to a second side of goggle frame 30 on a first end and to a second pulley 70 on a second end, cable housings 64 are mounted to the inside of helmet 20, cable spool 54 and cable adjustment knob 50 are rotationally mounted preferably to a front portion of helmet 20 (such as near the "mouth" area of helmet 20), and cable 60 is wound around cable spool 54, passed through cable housings 64, and around both of pulleys 70.

In practice, a user dons helmet 20 and positions breath deflector 40 near his eyes, nose, and mouth with deflector skirt 44 preferably removably attached (e.g. via a hook & loop connection) to a forward portion of helmet 20. The user then rotates cable adjustment knob 50 in a tightening direction (which causes a payout length of cable 60 to decrease) such that breath deflector 40 comes to a comfortably snug contact to the user with elastic cords 76 being somewhat stretched. With breath deflector apparatus 10 so adjusted, the user can breathe while wearing the breath deflector apparatus without fogging a face shield of helmet 20, as the user's breathe is channeled away from a face shield of helmet 20. Moreover with breath deflector apparatus 10 so adjusted, the user may turn or move his head and the breath deflector remains in comfortably snug contact to the user even if there is some relative movement between the user's head and helmet 20. This is in distinct contrast to conventional breath deflectors which are readily dislodged or misadjusted when there is relative movement between the user's head and a helmet. Further, when a user desires to remove helmet 20, the user need merely pull out on adjustment knob 50 which allows tension in cable 60 to be relaxed (and causes a payout length of cable 60 to increase) such that breath deflector 40 is loosened from snug contact to the user. The user can then remove helmet 20 without necessarily removing goggle frame 30 from helmet 20. This is in distinct contrast to conventional goggles (which have a stretchable retention band) which must first be removed before a helmet may be removed.

In an alternate embodiment, breath deflector apparatus 10 is substantially identical to the preferred embodiment except that goggle frame 30 includes a lens therein. The lens may be a prescription or a non-prescription lens and may be a clear or a tinted lens. Goggle frame 30 may be specifically adapted so as to readily substitute one lens type for another lens type in goggle frame 30.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A breath deflector apparatus comprising a breath deflector, a helmet, a tether, a tether housing, a spool, eyewear, and an adjustment device, said breath deflector being connected to said eyewear and tethered to said spool and said adjustment device by said tether, and said adjustment device being mounted to a front portion of said helmet, and wherein said apparatus is adapted such that a first actuation of said adjustment device causes a first rotation of said spool, movement of said tether through said tether housing, and a payout length of said tether to decrease and such that a second actuation of said adjustment device causes a second rotation of said spool, movement of said tether through said tether housing, and a payout length of said tether to increase.

2. The breath deflector apparatus of claim 1, wherein when said apparatus is worn by a user and said breath deflector is in comfortably snug breath deflecting contact with said user, movement of said user's head relative to said helmet, does not cause said breath deflector to release from said comfortably snug breath deflecting contact with said user.

3. The breath deflector apparatus of claim 1, wherein said helmet defines a snowmobile helmet.

4. The breath deflector apparatus of claim 1, wherein said apparatus includes at least one elastic member connecting a goggle frame to a cable.

5. The breath deflector apparatus of claim 1, wherein said apparatus includes at least one pulley connecting a goggle frame to a cable.

6. The breath deflector apparatus of claim 1, wherein said eyewear comprises at least one of a goggle frame having a lens, and a goggle frame having no lens.

7. The breath deflector apparatus of claim 6, wherein said lens defines at least one of a tinted lens, an untinted lens, a prescription lens, a non-prescription lens, and a combination thereof.

8. A breath deflector apparatus comprising a breath deflector connected to a goggle frame, a tether, a tether housing, a spool, eyewear, and an adjustment device having an adjustment knob, wherein said breath deflector is connected to said eyewear and tethered to said spool and said adjustment device by said tether, and wherein said apparatus is adapted such that rotation of said adjustment knob in a first direction causes a first rotation of said spool, movement of said tether through said tether housing, and a payout length of said tether to decrease and such that linear movement of said adjustment knob in a second direction causes a second rotation of said spool, movement of said tether through said tether housing, and a payout length of said tether to increase.

9. The breath deflector apparatus of claim 8, wherein when said apparatus is worn by a user and said breath deflector is in comfortably snug breath deflecting contact with said user, movement of said user's head does not cause said breath deflector to release from said comfortably snug breath deflecting contact with said user.

10. The breath deflector apparatus of claim 8, wherein said apparatus comprises a helmet having said adjustment knob mounted to a front portion thereof.

11. The breath deflector apparatus of claim 8, wherein said apparatus comprises at least one elastic member connecting said breath deflector to said tether.

12. The breath deflector apparatus of claim 8, wherein said apparatus comprises at least one pulley connecting said breath deflector to said tether.

13. The breath deflector apparatus of claim 8, wherein said eyewear comprises at least one of a goggle frame having a lens, and a goggle frame having no lens.

14. The breath deflector apparatus of claim 13, wherein said lens defines at least one of a tinted lens, an untinted lens, a prescription lens, a non-prescription lens, and a combination thereof.

15. A breath deflector apparatus comprising a breath deflector, a tether, a tether housing, a spool, eyewear, and an adjustment device having a rotatable knob, wherein said breath deflector is connected to said eyewear and tethered to said spool and said adjustment device by said tether, and wherein said apparatus is adapted such that a first actuation of said adjustment device causes a first rotation of said spool, movement of said tether through said tether housing, and a payout length of said tether to decrease and such that a second actuation of said adjustment device causes a second rotation of said spool, movement of said tether through said tether housing, and a payout length of said tether to increase, and wherein one of said first actuation and second actuation comprises a rotation of said rotatable knob and another of said first actuation and second actuation comprises a linear movement of said rotatable knob.

16. The breath deflector apparatus of claim 15, wherein when said apparatus is worn by a user and said breath deflector is in comfortably snug breath deflecting contact with said user, movement of said user's head does not cause said breath deflector to release from said comfortably snug breath deflecting contact with said user.

17. The breath deflector apparatus of claim 15, wherein said apparatus comprises a helmet having said rotatable knob mounted to a front portion thereof.

18. The breath deflector apparatus of claim 15, wherein said apparatus includes at least one of an elastic member and a pulley connecting said breath deflector to said tether.

19. The breath deflector apparatus of claim 15, wherein said eyewear comprises at least one of a goggle frame having a lens, and a goggle frame having no lens.

20. The breath deflector apparatus of claim 19, wherein said lens defines at least one of a tinted lens, an untinted lens, a prescription lens, a non-prescription lens, and a combination thereof.

* * * * *